United States Patent [19]
Nevin et al.

[11] Patent Number: 5,655,253
[45] Date of Patent: Aug. 12, 1997

[54] BENCH TOP DUST COLLECTOR

[76] Inventors: Robert L. Nevin, 14850 Sunny La., Orland Park, Ill. 60462; Denis M. Sexton, 15112 Acorn La., Lockport, Ill. 60441

[21] Appl. No.: 645,433

[22] Filed: May 13, 1996

[51] Int. Cl.⁶ .................................................. A47L 5/38
[52] U.S. Cl. .................. 15/310; 15/319; 15/324; 15/339
[58] Field of Search ........................ 15/310, 319, 339, 15/324, 301

[56] References Cited

U.S. PATENT DOCUMENTS

| | | |
|---|---|---|
| 1,267,091 | 5/1918 | Leiman . |
| 3,066,345 | 12/1962 | Kasper . |
| 3,786,531 | 1/1974 | Borg ............................................ 15/310 |
| 4,594,747 | 6/1986 | Dempsey ...................................... 15/301 |
| 4,607,413 | 8/1986 | Schmidt et al. ........................... 15/310 X |
| 4,947,510 | 8/1990 | English . |
| 5,271,123 | 12/1993 | Teske . |

FOREIGN PATENT DOCUMENTS 504185  4/1939  United Kingdom .................... 15/319

*Primary Examiner*—Chris K. Moore
*Attorney, Agent, or Firm*—Knechtel, Demeur & Samlan

[57] ABSTRACT

A self-contained portable device for collecting dust and other particulate matter or the like. There is a housing with partially open sides sufficiently large to allow the entrance of an operator's hands. A sensor is activated when the operator's hands are placed within the device. The sensor activates the vacuum motor and light source so that the work area is illuminated and particulate matter and dust can be drawn away from the work area. A removable and disposable filter bag collects the dust particles and can be disposed of when full. The operator does not come in contact with any contaminated dust or particulate matter in disposing of the filter bag.

16 Claims, 2 Drawing Sheets

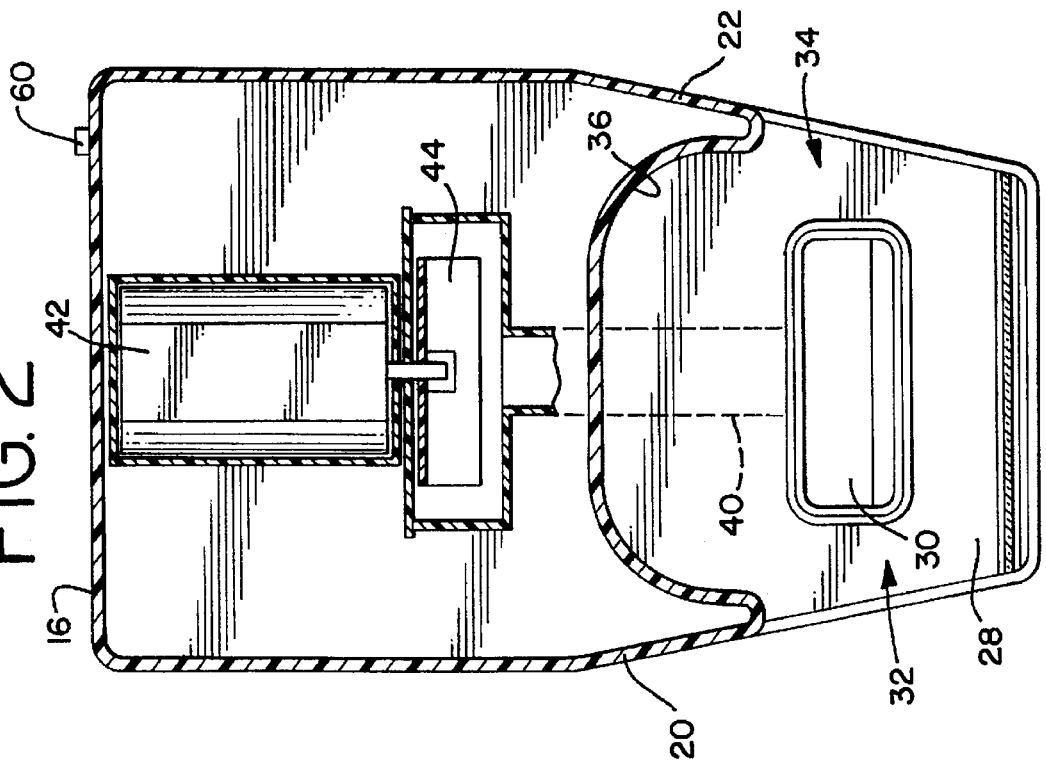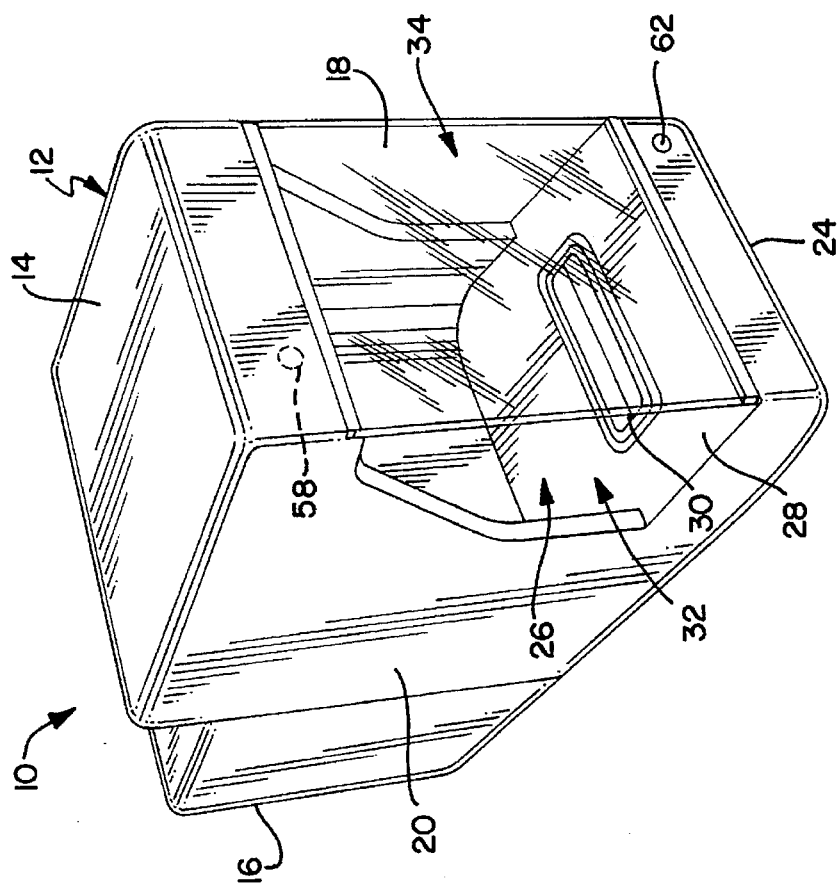

BENCH TOP DUST COLLECTOR

This invention relates to a dust vacuum collector and, more particularly, a dust vacuum collector adapted for use in the dental field.

BACKGROUND AND SUMMARY OF THE INVENTION

Quite often, a dentist must make final adjustments to various dental appliances such as crowns, bridges, dentures, orthodontic devices, and other restorations. When the dentist is making the final adjustments, he or she must continually try the appliance for fit in the patient's mouth, have the patient advise the dentist as to how the appliance feels, remove the appliance, and make any necessary modifications such that the appliance fits properly and comfortably. Every time the dentist makes an adjustment to the dental appliance, material is removed from the appliance. This is normally done by grinding with a hand piece. The material removed often falls on the dentist's lap, on the floor, on the patient, or is blown into the environment as dust. The dust and particulate are normally contaminated with the patient's saliva. This contaminates the environment which can spread potentially dangerous microorganisms. Obviously, it would be advantageous if the dust and particulate could be removed and collected in a safe and convenient manner.

Generally, the dentist removes the dental appliance and takes it to a remote area where the laboratory equipment is located. Adjustments are made to the dental appliance and the dentist comes back into the treatment room and places the dental appliance back in the patient's mouth. This process may be repeated several times until the proper fit is achieved. Each time, the dentist leaves the treatment room and goes to the laboratory area to do the adjustments. Obviously, this is time consuming and inconvenient. Furthermore, the greater distance the dentist must travel to the laboratory and the more objects he or she touches, the greater the likelihood of cross-contamination in the office environment.

The prior art has addressed the problem of collecting dust from a work surface. For example, U.S. Pat. No. 1,267,091 illustrates a somewhat conventional design for a dust collector which draws the dust from the work surface into a compartment below the work surface. This device does not offer the advantages of automatic energization of the dust collecting unit without the need of the operator touching switches in order to activate it. Furthermore, this device is not portable and would generally be set up in a laboratory remote from the examination room.

U.S. Pat. No. 3,066,345 illustrates a blackboard eraser cleaner which is a dust collecting device. The device does not allow for hands-free operation, does not illuminate the work piece, and does not have a hood or a safety shield to protect the operator from the dust.

U.S. Pat. No. 5,271,123 illustrates an apparatus for cleaning porcelain work pieces. This device has a canister which has a top work surface and a central opening through which air is drawn. This draws the dust particles into a dust bag. However, this device must be connected to a separate vacuum source and is not self-contained. There is no hood or protection for the operator nor does it allow for hands-free operation but requires the operator to turn switches on and off.

U.S. Pat. No. 4,947,510 illustrates a small vacuum box which is used for collecting particulate from wooden work pieces. However, this is adaptable for other uses. The device has a cabinet-like design which includes partially enclosed sides and an enclosed top and back. There is a partial glass shield in front to protect the operator. A fan in the rear of the unit provides for air flow to draw the particulate into a compartment. This compartment or collection box can be removed such that the collected particles can be disposed of. One shortcoming of the '510 device is that it does not collect contaminated particles in a removable and disposable filter bag. Thus, the possibility of spreading potentially harmful microorganisms through coming in contact with collected particles is still present. A second shortcoming of the '510 device is that it requires the operator to turn the device on and off manually through the use of electrical switches. In the dental field, the operator may contact the switches which can be contaminated which increases the likelihood of cross-contamination.

Applicant's invention comprises a self-contained portable device for collecting dust and particles from dental appliances as the same are being worked upon in the treatment room. Thus, there is no need for the dentist to leave the patient area. The device is self-contained and portable such that the dentist can have a dust-collecting device in each treatment area. The device has a housing which is enclosed except for partially opened sides which are sufficiently opened such that the dentist's hands can pass through them. There is a hollow work chamber in the front of the unit. The front of the chamber has a removable glass or plastic shield which protects the dentist from dust or particles which are removed from the dental appliance during the adjustment operation. The safety shield is removable to allow access to the chamber for cleaning and disinfecting. At the bottom of the chamber is a vacuum duct which draws the air and dust particles through a conduit into a filter bag. The filter bag is removed and disposed of when filled. When the operator places his hands into the work chamber, a sensor automatically turns on the fan motor to create a vacuum at the vacuum duct and also energizes a light within the chamber to illuminate the work area. Thus, the operator does not have to manually turn on any additional switches or come in contact with any such switches before working on the work piece.

OBJECTS AND ADVANTAGE

Thus, it is an object of the invention to provide a self-contained portable device for collecting dust particles or the like which also protects the operator, patient, and other office personnel from contaminated dust particles which are emitted into the atmosphere. It is a related object to provide a vacuum chamber which removes the dust particles and stores them in a filter bag. A related object is the object of having an easily removable and disposable filter bag which can be discarded after it is filled.

Yet, another object is the object of having a dust collecting device which automatically turns on when the operator places his or her hands within a work chamber such that the operator does not have to touch any switches to activate the unit.

These and other objects will become apparent upon reading the detailed description of the drawings and description of the preferred embodiment.

DETAILED DESCRIPTION OF THE DRAWINGS

FIG. 1 is a perspective view of a self-contained portable device for collecting dust particles.

FIG. 2 is a top cross-sectional view of the device of FIG. 1.

DESCRIPTION OF THE PREFERRED EMBODIMENT

Figure 3:
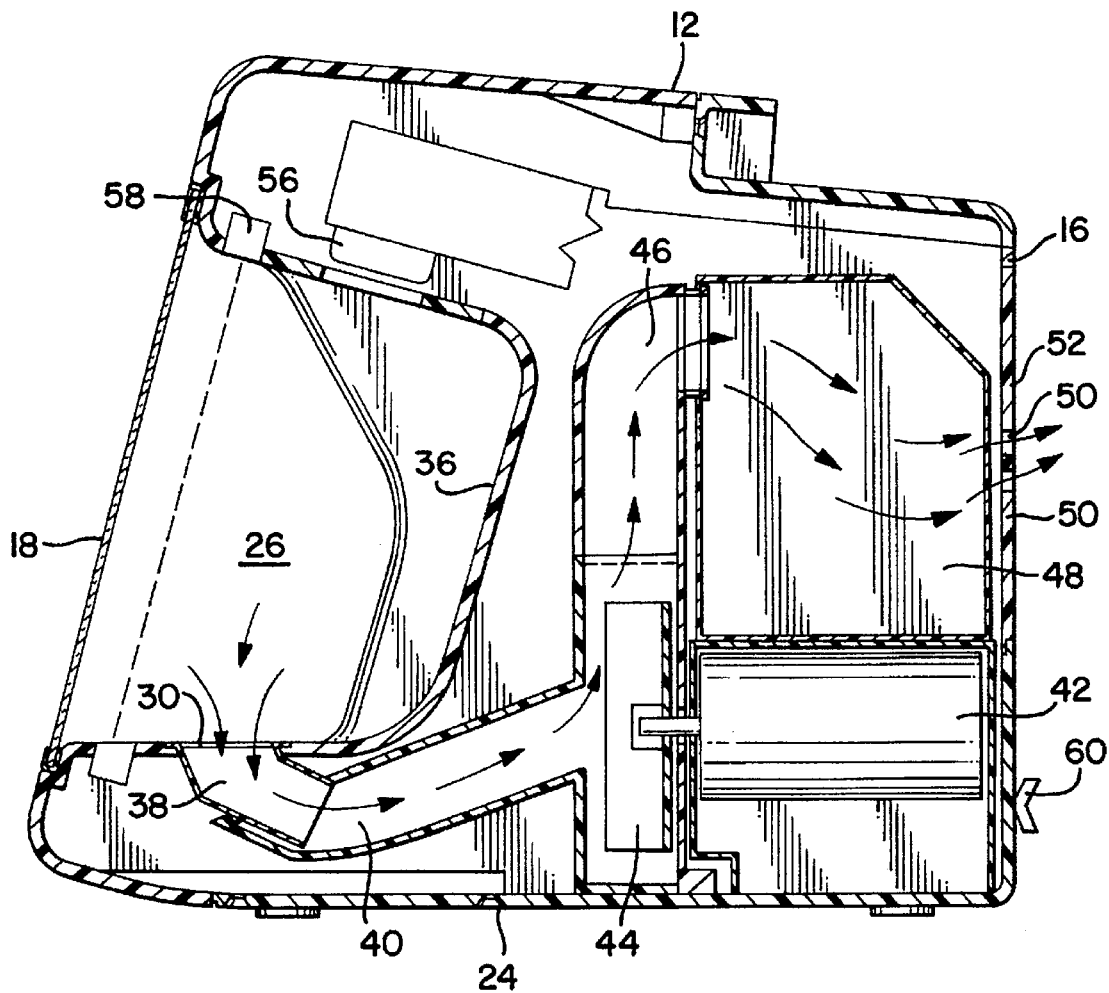
FIG. 3 is a side-elevational view in cross section of the device of FIG. 1.

Turning first to FIG. 1, there is illustrated a self-contained portable device for collecting dust particles or the like 10. Such a device is particularly well suited for the collection of dust and contaminates generated when a dentist is working on a dental appliance such as a denture, crown, bridge, implant, or orthodontic appliance, etc. (hereinafter referred to as an "appliance" or "dental appliance") that will properly fit in the patient's mouth. Often, minor adjustments must be made in the appliance so that it will fit without patient discomfort. These minor adjustments are normally made in the dentist's office and normally are done when the appliance is inserted and removed several times while trying to achieve the perfect fit.

The device 10 has an outer housing 12. The housing 12 is comprised of a top 14, a rear 16, a front 18, a left side 20, a right side 22, and a bottom 24. Generally, the front 18 has a removable clear plastic shield or tempered glass through which the operator can see into a work chamber 26. Although not illustrated, the front 18 can have a magnifying glass or similar device attached to it so that the operator can more easily observe and work on the details of the appliance. Adjacent the bottom 24 is a base plate 28 which has a vacuum duct 30 disposed therein. The left side 20 has a left hand opening 32 and the right side has a right hand opening 34. The left and right hand openings 32, 34 are defined by a cutout portion of the left and right sides 20, 22. The openings 32 and 34 are of sufficient size to permit the operators hands to enter into the work chamber 26 so that the operator can modify the dental appliance.

Turning to FIG. 3, the internal workings of the dust-collecting device are illustrated. The work chamber 26 is defined between the front 18 and a work chamber rear wall 36. The rear wall 36 is somewhat concave in shape (as seen in FIG. 2). This shape improves air flow and avoids any sharp corners in which dust and contaminates can lodge and allows the rear wall 36 to be easily cleaned. In the base plate 28 is the vacuum duct 30 which is connected to a vacuum chamber 38. This, in turn, is connected to a vacuum passageway 40. There is a vacuum-forming device comprised of a direct current motor 42 which drives a fan blade 44. The fan blade is in fluid communication with the vacuum passageway 40 to draw a vacuum from the vacuum duct 30. The fan blade 44 discharges into a positive pressure chamber 46 which, in turn, is connected to a filter bag 48 at the rear of the housing 12.

The filter bag is preferably a non-woven material which will capture particles as small as 0.1 microns. This will trap most bacteria. There are air vent holes 50 at the rear 16 of the housing 12 which permits the positive air flow to leave the filter bag 48 and exit the rear 16. There is a removable rear door 52 at the rear of the housing 16. This permits the user to have access to the filter bag 48 which can be removed when it is filled. By containing the dust particulate and other contaminates within the filter bag 48, the user never comes in contact with the contaminated particles.

Also, as can be seen in FIG. 3, there is a work light 56 which illuminates the work chamber 26. There is also an electric eye and sensor 58 located at the top of the chamber 26. When the operator places his or her hand through the hand opening 34, he or she breaks the beam from the electric eye 58. This energizes the work light 56 and motor 42.

Figure 4:
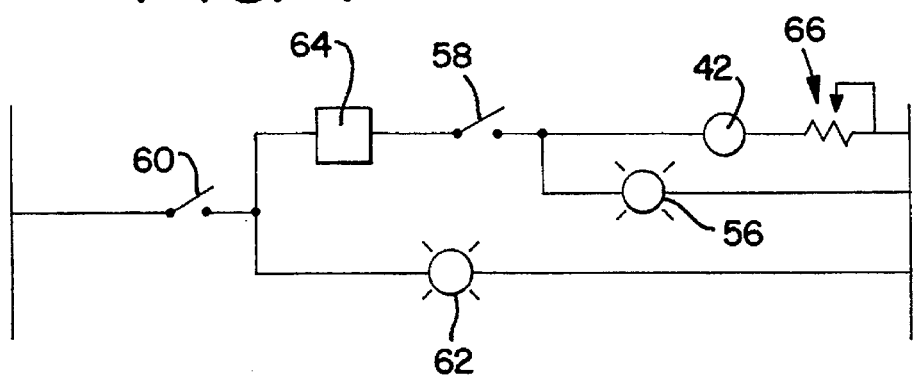
FIG. 4 is a schematic view of the electronic circuitry of the inventive device.

The circuitry is more clearly illustrated in FIG. 4. There is an "on/off" switch 60 located at the back of the unit. When the switch 60 is pushed to the "on" position, a "power on" light 62 is energized at the front of the unit indicating that there is power to the device 10. A converter 64 converts the 120 volts AC input to a 12 volt DC output. The electric eye 58 is connected to the converter 64. When the electric eye 58 is interrupted, its contact closes. This energizes the motor 42. A rheostat 66 controls the motor speed thereby controlling the amount of vacuum drawn at the vacuum duct 30. The work light 56 is also energized when the electric eye contact closes. Thus, light is provided to the interior of the work chamber 26.

The operator's hands need not touch any other switches once the device is energized by activating switch 60, such that the operator can work on a dental appliance within the work chamber 26 while the fan motor, vacuum, and light source are all energized automatically. The vacuum drawn at the duct 30 removes particles generated from working on the dental appliance and draws them into the disposable filter bag 48. The operator removes the filter bag 48 when the bag is filled. In this manner, the operator never comes in contact with contaminated particulate. The device also minimizes the possibility of the operator transmitting potentially contaminated microorganisms into the patient's mouth, as the operator does not touch any contaminated switches or objects while moving the dental appliance from the work chamber 26 to the patient's mouth and back again.

As the device is completely self-contained and portable, the operator can move it from one work area to another. By virtue of the fact that a centralized vacuum source need not be utilized such as the prior art discloses, the need to move the dental appliance to a centralized location having a central vacuum source is no longer required.

Thus, there has been provided a self-contained portable device for collecting dust particulate or the like that fully satisfies the objects, aims and advantages set forth herein. While the invention has been described in conjunction with a specific embodiment, it is evident that many alternatives, modifications and variations will be apparent to those skilled in the art in light of the foregoing description. Accordingly, it is intended to embrace all such alternatives, modifications and variations as fall within the spirit and scope of the appended claims.

What is claimed is:

1. A self-contained portable device for collecting dust particulate from dental appliances or the like comprising:

a housing having a front, a rear, a top, a bottom, and at least partially open sides, the open sides having openings of sufficient size to receive an operator's hands therethrough;

a hollow work chamber disposed at the front of the housing;

a base plate at the bottom of the hollow work chamber;

a vacuum duct in the base plate;

vacuum means fluidly connected to the vacuum duct to draw a vacuum at the vacuum duct in the base plate;

a filter bag disposed within the housing for collecting and containing particulate drawn from the vacuum duct;

light means to illuminate the work chamber;

sensor means for detecting the presence of the operator's hands within the hollow work chamber, the sensor means sending an electrical signal responsive to the presence of the operator's hands in the work chamber;

means responsive to the electrical signal to energize the light and the vacuum means;

whereby when the operators hands are inserted into the chamber, the sensor means detects their presence, energizing the light and vacuum means, thus drawing a vacuum at the vacuum duct to remove dust particulate from the work chamber.

2. The device of claim 1 wherein the vacuum means comprises a motor connected to a fan, the fan creating a vacuum at the vacuum duct, and the fan discharging the air flow from the vacuum duct into the filter bag, with air vent holes disposed at the rear of the housing to allow the air from the filter bag to be discharged.

3. The device of claim 2 and further comprising a door at the rear of the housing to allow access to the filter bag so that it can be removed and disposed of when full.

4. The device of claim 2 wherein the motor is a variable speed motor to control the amount of vacuum drawn at the air duct.

5. The device of claim 1 and further comprising a removable clear plastic or tempered glass safety shield at the front of the housing to shield the operator from particulate which may be discharged from the hollow work chamber.

6. The device of claim 1 wherein the hollow work area has a contour which directs the air flow towards the duct.

7. The device of claim 6 wherein the hollow work area is concave.

8. The device of claim 1 wherein the sensor means is a photo-electric light and sensor which sends the signal when the operator breaks the beam of light received by the sensor.

9. A self-contained portable device for collecting dust and other particulate matter or the like comprising:

a housing having a front, a rear, a top, a bottom, and partially open sides sufficiently large to allow an operator's hands to pass therethrough;

a hollow work chamber defined by the front, rear, top, bottom, and sides wherein the operator can work on dental appliances;

a duct at the bottom of the hollow work chamber;

a disposable filter bag within the housing, the duct in fluid communication with the filter bag;

means for creating a vacuum at the duct for drawing the dust and particulate matter from the hollow work chamber to the filter bag where it is contained;

sensor means for detecting the presence of the operator's hands in the work chamber, the sensor means operatively connected to the means for creating a vacuum, the means for creating a vacuum being automatically activated when the operator's hands are placed in the work chamber.

10. The device of claim 9 and further comprising a light source in the chamber, the light source operatively connected to the sensor means to be automatically activated when the operator's hands are placed in the work chamber.

11. The device of claim 9 wherein the means for creating a vacuum comprises a motor connected to a fan, the fan creating a vacuum at the duct, and the fan discharging the air flow from the duct into the filter bag, with air vent holes disposed at the rear of the housing to allow the air from the filter bag to be discharged.

12. The device of claim 11 and further comprising a door at the rear of the housing to allow access to the filter bag so that it can be removed and disposed of when full.

13. The device of claim 9 and further comprising a clear plastic or tempered glass safety shield at the front of the housing to shield the operator from particulate which may be discharged from the hollow work chamber.

14. The device of claim 9 wherein the hollow work area has a contour which directs the air flow towards the duct.

15. The device of claim 9 wherein the sensor means is a photo-electric light and sensor which sends the signal when the operator breaks the beam of light received by the sensor.

16. The device of claim 9 wherein the motor is a variable speed motor to control the amount of vacuum drawn at the air duct.

* * * * *